United States Patent [19]

Crow

[11] Patent Number: 4,855,668
[45] Date of Patent: Aug. 8, 1989

[54] FLEXIBLE PROBE AND SAMPLING DEVICE FOR CORROSION MEASURING

[76] Inventor: Stanley Crow, 121 Easy St., Livingston, Tex. 77351

[21] Appl. No.: 92,716

[22] Filed: Sep. 3, 1987

[51] Int. Cl.$^4$ .................. G01R 27/22; G01N 1/10
[52] U.S. Cl. .................. 324/65 CR; 324/65 P; 324/71.2; 73/863.86
[58] Field of Search .............. 324/65 CR, 65 P, 65 R, 324/71.1, 71.2, 158 P, 149; 73/86, 863.81, 863.85, 863.86, 864.73; 204/1 C, 404

[56] References Cited

U.S. PATENT DOCUMENTS

| | | | |
|---|---|---|---|
| 3,320,570 | 5/1967 | Lied, Jr. | 324/65 CR |
| 4,101,828 | 7/1978 | Dehler | 324 CR/65 CR X |
| 4,338,563 | 7/1982 | Rhoades et al. | 324/65 CR |
| 4,410,885 | 10/1983 | Stenstrom | 324/65 P X |

Primary Examiner—Reinhard J. Eisenzopf
Assistant Examiner—Jack B. Harvey
Attorney, Agent, or Firm—Bernard A. Reiter; Mark G. Bocchetti

[57] ABSTRACT

A combination corrosion probe and sampling device. The probe is flexible such that it can be inserted into a piece of operating equipment such as a distillation column and reach tray surfaces or the like which heretofore have been difficult, if not impossible, to reach with a probe. The probe allows the measurement of the rate of corrosion over a period of time and further includes a thermocouple and temperature compensation means to assure the accuracy of the amount of corrosion measured. The flexibility of the probe is enabled by a portion of the probe being fabricated from a pliant substantially cylindrical member such as a ribbed cable protector. A capillary tube runs substantially the length of the probe having an open end in close proximity to the location where corrosion is being measured. That capillary tube runs to a sampling valve near the opposite end of the probe. This enables the sampling of the process fluid at the location where measurements are being taken so that laboratory tests will show precisely what operating conditions exist at that point.

9 Claims, 2 Drawing Sheets

FLEXIBLE PROBE AND SAMPLING DEVICE FOR CORROSION MEASURING

BACKGROUND OF THE INVENTION

1. Field of the Invention

The present invention relates generally to probe and sampling devices and more particularly to flexible probe and, sampling devices for use in measuring corrosion levels on trays within fractionating columns used in the petrochemical and refining industries.

2. Brief Description of the Prior Art

Refineries and chemical plants have long experienced problems with corrosion of trays within distillation columns. Corrosion typically occurs at specific temperatures related to the water dew point in the system.

The measurement of the amount of corrosion individual trays are experiencing within a distillation column is of tantamount importance in maintaining the column within optimum operating limits. Tray corrosion can cause a loss of tray efficiency. Ultimately, tray failure may occur resulting in a severe loss of column efficiency.

Electrical resistance probes for measuring corrosion in refinery process equipment have been in use for many years. Heretofore, the probes have been of the straight and rigid type having a basic rodlike structure. These conventional probes as previously used make it difficult if not impossible to access certain areas where corrosion is known to exist. In particular, it is extremely difficult to insert such a probe within a distillation column in a refinery or chemical plant such that the probe can measure corrosion of a specific tray within the distillation column. In order to use such a probe, it is necessary to tap the distillation column above a particular tray on which corrosion is to be measured. The tap must be performed at an angle which converges with the plane of the tray to allow the straight probe to contact the particular tray.

Besides the structural deficiencies of the probes of the prior art, they are also deficient in other respects. Meaningful corrosion measurement is dependent upon accurate temperature measurement and temperature compensation at a place where the corrosion is occurring. It should be recognized that, typically, corrosion measurement probes measure corrosion as a function of electrical resistance and resistance is affected by temperature. The probes heretofore used do not incorporate any rapid temperature compensation in the probe circuitry. Neither do the probes of the prior art have the ability to measure temperature with a thermocouple at the probe extremity.

It is also noted that the probes of the prior art do not incorporate any sampling means. The ability to take a sample of the process fluid at the point where corrosion is being measured is extremely beneficial. It allows the operators to determine precisely what is occurring at that tray level thereby providing precise data upon which to base adjustments to the operating conditions of the distillation column such that further corrosion can be prevented or slowed.

SUMMARY OF THE INVENTION

It is therefore an object of the present invention to provide a probe of flexible structure for measuring corrosion of trays within distillation columns.

Another object of the present invention is to provide a flexible corrosion measuring probe which has incorporated therein rapid temperature compensation circuitry.

A further object of the present invention is to provide a flexible probe for measuring corrosion which has the ability to measure temperature at the probe extremity.

Yet another object of the present invention is to provide a flexible probe device for measuring corrosion which has the ability to take samples of the process fluid from the point where corrosion is being measured.

Briefly stated, the foregoing and numerous other features, objects and advantages of the present invention will become readily apparent upon a reading of the detailed description, claims and drawings set forth hereinafter. These features, objects and advantages are accomplished by constructing a portion of the probe device with a flexible, ribbed cable protector. That portion of the probe device enclosed in the flexible, ribbed cable protector is therefore pliant. This flexibility allows the probe to be inserted through a packing gland mounted to a full port valve. The full port valve may be one already present as can be typically found on tower manways at various locations throughout the height of the tower. If a three quarter inch full port valve is not available, such a valve can be either hot tapped through the manway or through the vessel wall during operation of the tower. Alternatively, the tower can be modified to have such a valve mounted thereon when the tower is not in operation and has been purged.

The flexibility of the probe allows the tap and valve to be mounted such that it projects radially and perpendicularly from the cylindrical body of the distillation column. The probe, once inserted through the valve will bend downward under its own weight to come in contact with the tray surface. This is a significant advantage over the prior art and the problems encountered with using rigid type probes.

The probe device of the present invention further includes a thermocouple positioned at the probe extremity to accurately measure temperature at the location where corrosion is being measured. This thermocouple in combination with the bridge circuitry of the probe (designed to give accurate temperature compensation) gives meaningful and accurate measurement of corrosion.

It should be understood that the determination of the amount of corrosion present is accomplished by the measurement of resistance through part of the bridge circuit of the probe. That part of the bridge circuit is constructed of a material which duplicates the tray material within the distillation column. As that part of the bridge circuit deteriorates due to corrosion over a period of time, the resistance through that part of the bridge circuit increases. Because the probe is in close proximity to the tray, the corrosion suffered by that part of the bridge circuit exposed to the process fluid will duplicate the corrosion suffered by the tray itself.

The extremity of the probe which is inserted into the distillation column includes a protective guard which is present to prevent damage which could be caused by abrasion or bumping of that part of the circuitry which is exposed to the process fluid.

That part of the circuitry which is exposed extends from a cylindrical member which is sealed with a corrosion resistant material thereby acting as a plug to prevent the passing of process fluid into the structure of the probe itself.

The probe circuitry, including the circuitry for the thermocouple and temperature compensation terminate at a typical six prong plug located at the opposite end of the probe device which remains outside of the distillation column. With the use of this six probe prong, the probe is connected electronically to one of the known corrosion meters which monitors corrosion by measuring electrical resistance. One such corrosion meter is the T-N 4300 Model CK-3 Corrosometer as manufactured by Rohrback Instruments. The thermocouple can be read with any instrument typically used for reading thermocouples. Such instruments include the Omega 871 for type K series thermocouples and the Omega 872 for type J series thermocouples, as manufactured by Omega Engineering, Inc.

The probe device of the present invention also incorporates a sampling capability. This is accomplished through the use of a capillary tube which passes through the sealed extremity of the probe such that it is exposed to the process fluid. This flexible capillary tube passes through the length of the probe such that a sample can be taken through a small valve mounted on the opposite end of the probe. This sampling capability allows the accumulation of precise data on the exact operating conditions present where corrosion is being measured.

FIG. a detailed elevation view of the distal end of the probe.

DETAILED DESCRIPTION OF THE PREFERRED EMBODIMENT

Figure 1:
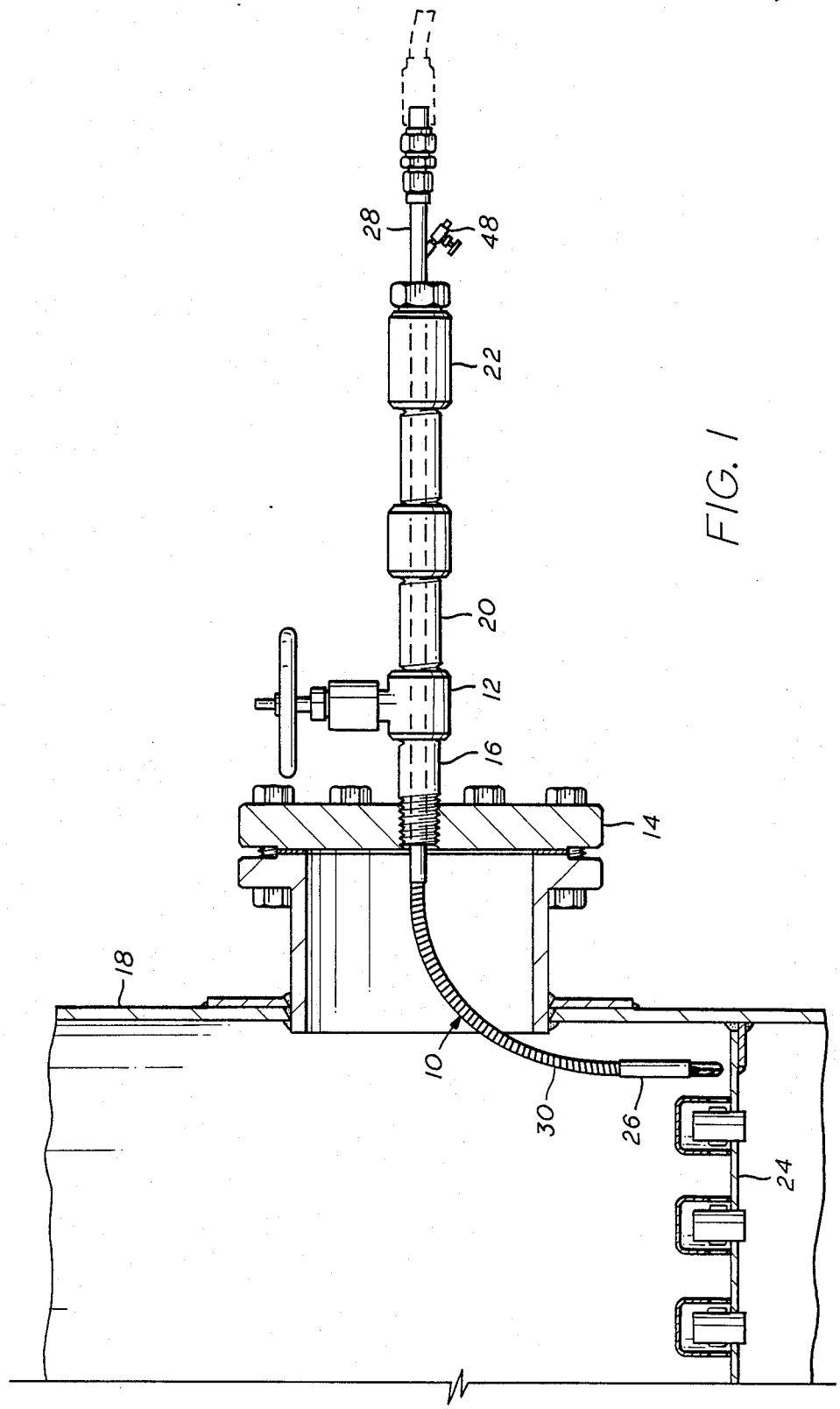
FIG. 1 is a side elevation of the probe device of the present invention inserted through a full port valve mounted on a manway of a distillation column.

Turning first to FIG. 1 there is shown combination flexible probe and sampling device 10 of the present invention extending through a full port valve 12 mounted to a manway 14 by means of nipple 16. Manway 14 is mounted to distillation column 18. Extending from full port valve 12 is conduit 20 which has attached thereto packing gland 22. The use of packing gland 22 allows the flexible probe 10 to be inserted therethrough up to valve 12. When so positioned, the combination probe and sampling device 10 is in fluid tight position within the packing gland 22 such that the full port valve 12 can then be opened. This allows the flexible probe and sampling device 10 to pass through valve 12 and be positioned in close proximity to the tray 24 where corrosion is to be measured.

Figure 2:
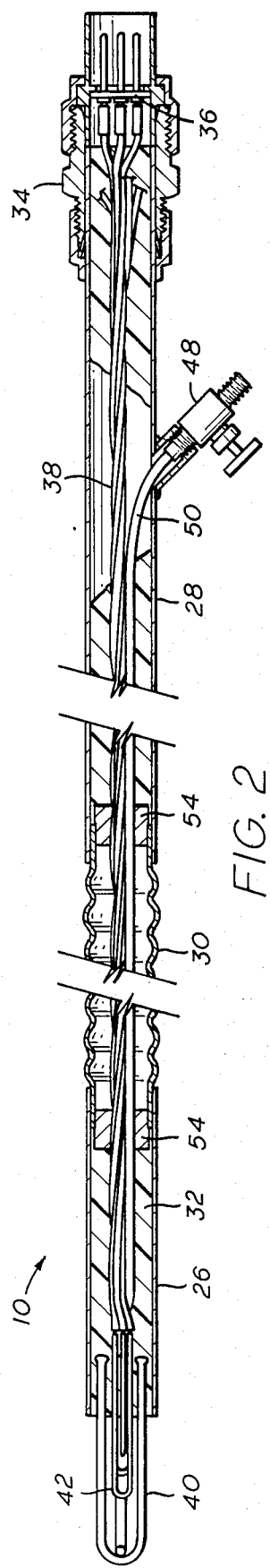
FIG. 2 is a side elevation of the combination probe and sampling device of the present invention.

As best shown in FIG. 2 the flexible probe and sampling device 10 of the present invention is divided into three major segments, two of which are rigid and one being flexible. The rigid segments are cylindrical members 26 and 28. Cylindrical members 26 and 28 are, in actuality, pipe or tubing and can be manufactured from any material suitable for the environment within the tower. Such materials include stainless steel, monel and a variety of other alloys. Connecting cylindrical members 26 and 28 is flexible member 30. Flexible member 30 is a ribbed cable protector which may be manufactured from stainless steel, steel, Teflon ®, monel or any other suitable material depending upon the process in which the flexible probe and sampling device of the present invention is to be used. If stainless steel or some other metal is used to fabricate flexible member 30, such flexible member will have a continuous spiral seam through which the process fluid could enter flexible member 30. This can be prevented by including a flexible Teflon ® sheath within flexible member 30.

If Teflon ® is used to fabricate the ribbed cable connector type structure of flexible member 30, such flexible member 30 can be fabricated as a continuous flexible tube which will have no seams through which process fluid will leak. However, because the strength of a flexible member 30 fabricated from Teflon ® will not be as great as one fabricated from stainless steel, steel, monel or some other alloy, it may be necessary to add support cables within the ribbing of the Teflon ® ribbing to prevent structural failure of flexible member 30.

Rigid cylindrical member 26 is packed with a corrosion resistant sealing material. Such material must be non-conductive and non-porous and not subject to corrosion. Teflon ® may be used as the packing material 32 within cylindrical member 26. Some ceramics may also be used or some high temperature cement. One material found specifically effective for use as sealing material within cylindrical member 26 is Belzona Molecular Ceramic s-metal ®.

If flexible member 30 is constructed of steel or stainless steel, the connections between flexible member 30 and rigid cylindrical members 26 and 28 can be accomplished with silver solder. If the flexible member 30 is constructed of Teflon ®, the connection between flexible member 30 and rigid cylindrical members 26 and 28 can be accomplished with standard tube fittings, bushings and couplings. It should be understood that tube fittings and bushings could also be used when flexible member 30 is manufactured from stainless steel, steel, monel or some other alloy.

Connected to rigid cylindrical member 28 is tube coupling 34. Tube coupling 34 is preferably a swage-lok-like mechanical fitting. Mounted within coupling 34 is six prong plug 36. Extending from six prong plug 36 is wiring bundle 38. Wiring bundle 38 extends through flexible member 30 and into rigid cylindrical member 26. Mounted to rigid cylindrical member 26 and extending therefrom are guards 40 which are basically in the form of u-shaped solid metallic rods. Guards 40 are preferably coated with a corrosion resistant material to prevent their decay as may be caused by the environment within the distillation column. Extending through sealing material 32 and out of rigid cylindrical member 26 are bridge circuit portion 42, temperature compensation loop 44, and thermocouple 46.

Mounted radially to rigid cylindrical member 28 is a sampling valve 48. A flexible capillary tube 50 extends from sampling valve 48 through rigid cylindrical member 28, flexible member 30 and rigid cylindrical member 26 such that it has an open end positioned within guards 40 where it can receive process fluid such that the opening of sample valve 48 allows an operator to collect a process fluid sample taken precisely from the location where corrosion is being measured.

Once the combination flexible probe and sampling device of the present invention has been assembled, it is preferable to seal portions of rigid cylindrical member 28 in a manner similar to that by which rigid cylindrical member 26 is sealed. The purpose of sealing portions of rigid cylindrical member 28 is to prevent any possible flow of process fluid which may have leaked into flexible member 30 from passing through rigid cylindrical member 28 and coupling 34. To accomplish this, it will be necessary to drill and tap rigid cylindrical member 28 at a point near its connection to flexible member 30. The same non-conductive, non-porous, temperature resistant and corrosion resistant material used to pack rigid cylindrical member 26 can thus be used to pack the portion of rigid cylindrical member 28 near its connection to flexible member 30 There are plugs 54 positioned at the connections of flexible member 30 to rigid cylindrical members 26 and 28 to prevent the flow of the sealing material into flexible member 30 before the sealing material sets up. Similarly, coupling 34 may be drilled and provided with a tap such that sealing material can be packed into coupling 34 and extend into a portion of rigid cylindrical member 28. It is preferable that that portion of rigid cylindrical member 28 where sampling valve 48 is attached not be filled with sealing material.

Figure 3:
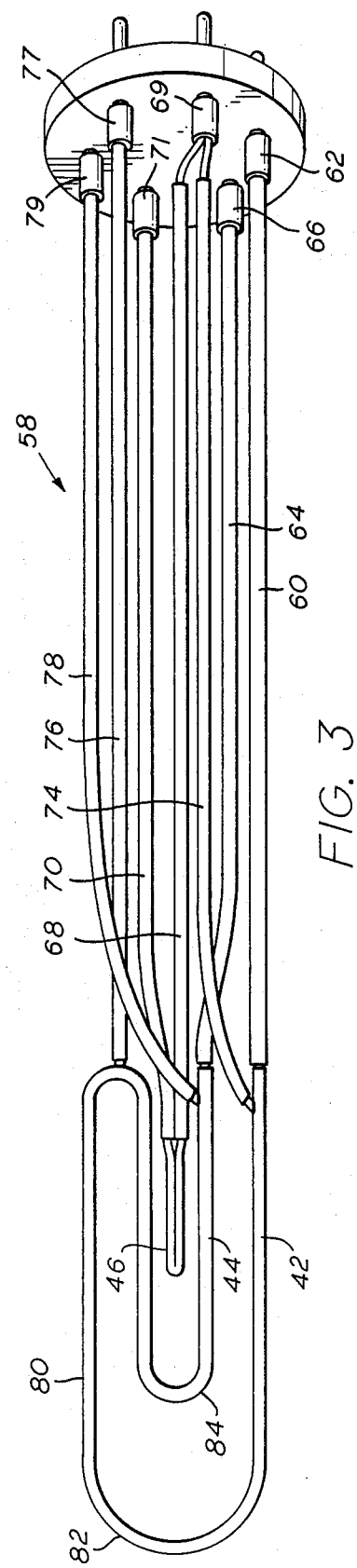
FIG. 3 is a wiring schematic of the circuitry of the combination probe and sampling device of the present invention.
Figure 4:
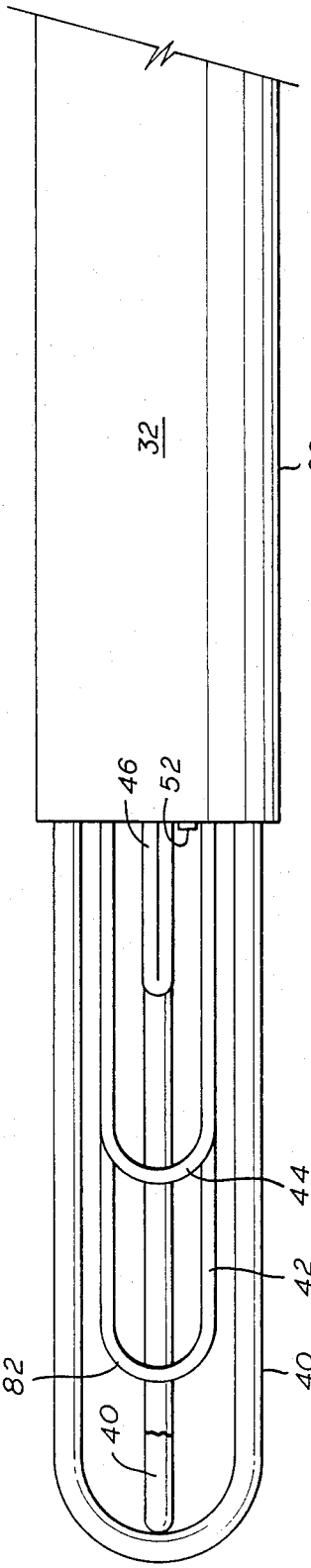

The circuit which allows the flexible probe and sampling device 10 of the present invention to measure electrical resistance and therefore, corrosion, as well as to compensate accurately for temperature is best depicted in FIG. 3. FIG. 3 shows a wiring schematic of the circuit as it extends from six prong plug 36. Conductor 60 of circuit 58 is a power wire and it extends from prong 62. Conductor 64 is also a power wire and it extends from prong 66. The thermocouple 46 is comprised of conductors 68 and 70 extending from prongs 69 and 71, respectively. The bridge circuit for measuring electrical resistance and therefore, the amount of corrosion, is comprised of conductors 74, 76 and 78 extending from prongs 69, 77 and 79, respectively.

There is a bridging conductor 80 which is electrically connected to power conductor 60, thermocouple conductor 74, bridge circuit conductor 76, bridge circuit conductor 78 and power conductor 64. Bridge circuit conductor 80 can be divided into an upper portion 82 and a lower portion 84. Upper portion 82 and lower portion 84 are that part of the circuit within the probe 10 which are exposed to the environment of the tower and, particularly, to the environment at the specific location where the probe is inserted such that when resistance is measured across bridging conductor 80, the amount of corrosion at that particular point is also measured. Temperature compensation is immediately and accurately provided by the inclusion of the lower portion 84 of the bridging conductor 80.

Thus, it can be seen that the flexible probe and sampling device of the present invention allows accurate measurement of corrosion within a piece of equipment which has heretofore been difficult if not impossible to reach with a conventional rigid-type probe. Further, the flexible probe and sampling device of the present invention allows temperature measurement, temperature compensation and sampling of the process fluid at the exact location where corrosion is being measured.

It should be understood that the probe of the present invention is to be used in measuring corrosion over a period of time. As the exposed portion of bridging conductor 80 corrodes over a period of time, its resistance will increase. The measurement of the increase in resistance is correlated to the amount of corrosion experienced over that same period of time. Because the metallurgy of the exposed portion of bridging conductor 80 duplicates the metallurgy of the surface where corrosion is suspected, the rate of corrosion for that surface will be substantially identical to the rate of corrosion for the exposed portion of bridging conductor 80.

From the foregoing, it will be seen that this invention is one well adapted to attain all of the ends and objects hereinabove set forth together with other advantages which are obvious and which are inherent to the apparatus.

It will be understood that certain features and subcombinations are of utility and may be employed with reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense.

What is claimed is:

1. A combination corrosion probe and sampling device comprising:
   a. a flexible substantially cylindrical member having proximal and distal ends;
   b. a first rigid substantially cylindrical member extending from said distal end of said flexible substantially cylindrical member;
   c. an electrical circuit passing through said first rigid substantially cylindrical member and said flexible substantially cylindrical member, a portion of said electrical circuit extending from said first rigid substantially cylindrical member thereby being exposed;
   d. sampling means passing through said first rigid substantially cylindrical member and said flexible substantially cylindrical member.

2. A combination corrosion probe and sampling device as recited in claim 1 further comprising:
   a thermocouple mounted within said first rigid substantially cylindrical member.

3. A combination corrosion probe and sampling device as recited in claim 1 further comprising:
   temperature compensation means connected to said electrical circuit and extending from said first rigid cylindrical member thereby being exposed.

4. A combination corrosion probe and sampling device as recited in claim 1 further comprising:
   a. a second rigid cylindrical member attached to said proximal end of said flexible substantially cylindrical member;
   b. coupling means mounted to said second rigid cylindrical member for electronically connecting said electrical circuit to a corrosion measuring device.

5. A combination corrosion probe and sampling device as recited in claim 1 wherein:
   said sampling means is comprised of a flexible capillary tube having a first end open and extending from said first rigid cylindrical member and a second end attached to a valve means mounted on said second rigid cylindrical member.

6. A probe for measuring corrosion within a piece of process equipment comprising:
   a. a flexible substantially cylindrical member having proximal and distal ends;
   b. a first rigid cylindrical member affixed to said distal end of said flexible substantially cylindrical member;
   c. a second rigid cylindrical member affixed to said proximal end of said flexible substantially cylindrical member;

d. an electrical circuit of known resistance mounted within said flexible substantially cylindrical member and said first and second rigid cylindrical members, a portion of said electrical circuit extending out from said first rigid cylindrical member thereby being exposed;

e. a thermocouple connected to said electrical circuit and mounted within said first rigid cylindrical member;

f. a capillary tube extending through said first rigid cylindrical member, said flexible substantially cylindrical member and said second rigid cylindrical member; and g. a sampling valve affixed to said capillary tube.

7. A probe for measuring corrosion within a piece of process equipment as recited in claim 6 wherein:

said electrical circuit includes a temperature compensation means.

8. A probe for measuring corrosion within a piece of process equipment as recited in claim 6 wherein:

said first rigid cylindrical member and said second rigid cylindrical member are sealed with a non-porous, non-conductive, corrosion resistant, temperature resistant material to prevent the passing of process fluids through said first and second rigid cylindrical members.

9. A probe for measuring corrosion within a piece of process equipment as recited in claim 6 further comprising:

coupling means mounted to said second rigid cylindrical member for electronically connecting said electrical circuit to a corrosion measuring device.

* * * * *